(12) United States Patent  
Gannoe et al.

(10) Patent No.: US 6,656,194 B1  
(45) Date of Patent: Dec. 2, 2003

(54) MAGNETIC ANCHORING DEVICES

(75) Inventors: Jamy Gannoe, Redwood City, CA (US); Craig Gerbi, Mountain View, CA (US)

(73) Assignee: Satiety, Inc., Palo Alto, CA (US)

(*) Notice: Subject to any disclaimer, the term of this patent is extended or adjusted under 35 U.S.C. 154(b) by 0 days.

(21) Appl. No.: 10/288,820

(22) Filed: Nov. 5, 2002

(51) Int. Cl.$^7$ .............................................. A61B 17/08
(52) U.S. Cl. .................................... 606/153; 604/96.01
(58) Field of Search ...................... 604/96.01; 606/153, 606/192

(56) References Cited

U.S. PATENT DOCUMENTS

| | | | | |
|---|---|---|---|---|
| 3,372,443 A | * | 3/1968 | Daddona ..................... 24/303 |
| 4,063,561 A | * | 12/1977 | McKenna .............. 128/207.15 |
| 4,258,705 A | | 3/1981 | Sorensen et al. | |
| 4,315,509 A | | 2/1982 | Smit | |
| 4,636,205 A | | 1/1987 | Steer | |
| 4,643,169 A | * | 2/1987 | Koss et al. .................... 600/31 |
| 4,671,287 A | * | 6/1987 | Fiddian-Green ............ 600/363 |
| 5,146,933 A | * | 9/1992 | Boyd ........................... 128/899 |
| 5,690,656 A | * | 11/1997 | Cope et al. ................. 606/153 |
| 5,904,147 A | * | 5/1999 | Conlan et al. .............. 128/899 |
| 6,293,923 B1 | * | 9/2001 | Yachia et al. ............. 604/96.01 |
| 6,352,543 B1 | * | 3/2002 | Cole ........................... 606/153 |
| 6,447,533 B1 | * | 9/2002 | Adams ........................ 606/213 |
| 6,535,764 B2 | * | 3/2003 | Imran et al. .................. 607/40 |
| 2002/0143347 A1 | * | 10/2002 | Cole et al. .................. 606/153 |
| 2002/0183768 A1 | * | 12/2002 | Deem et al. ................ 606/151 |

OTHER PUBLICATIONS

Grey, Henry; Anatomy of the Human Body, Williams & Wilkins, Thirtieth Amerian Edition, pp. 1466–1467.*

* cited by examiner

Primary Examiner—Michael J. Milano  
Assistant Examiner—Bradford C Pantuck  
(74) Attorney, Agent, or Firm—Morrison & Foerster LLP

(57) ABSTRACT

Magnetic anchoring devices are disclosed herein. Expandable devices that are inserted into the stomach of a patient are attached to its interior wall by magnetically coupling. Such expandable devices, like inflatable balloons, comprise at least one magnetic device, which may be a magnet, a magnetizable material, or a magnetic metal. The magnetic device may be positioned on the external or interior surface of the expandable device or may be integral thereto. The magnetic device is magnetically coupled to a magnetic anchor positioned on a surface of the stomach wall. In this way, the expandable devices are anchored to the stomach walls, preventing migration of the device to other areas of the body where they may become obstructions and pose health risks.

23 Claims, 10 Drawing Sheets

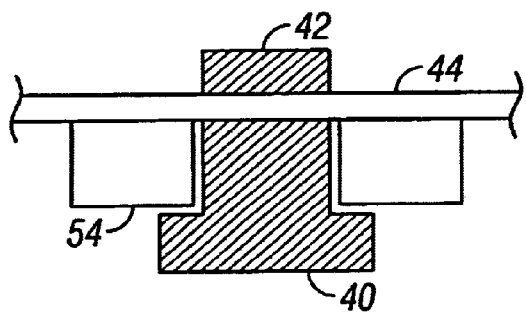
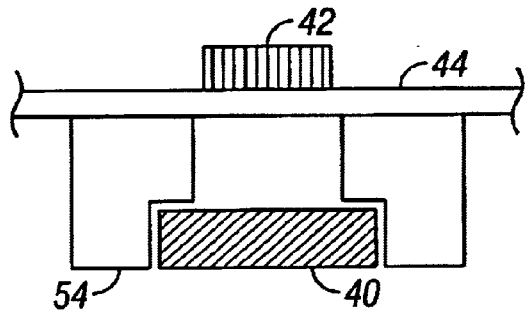
FIG. 5E    FIG. 5F
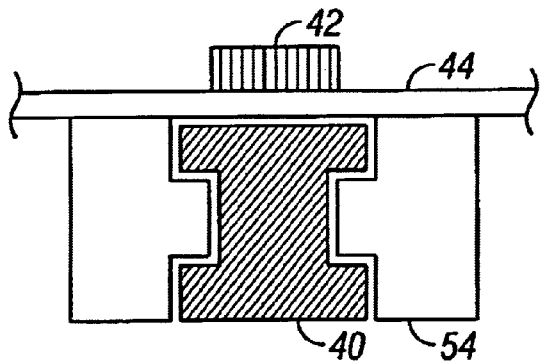
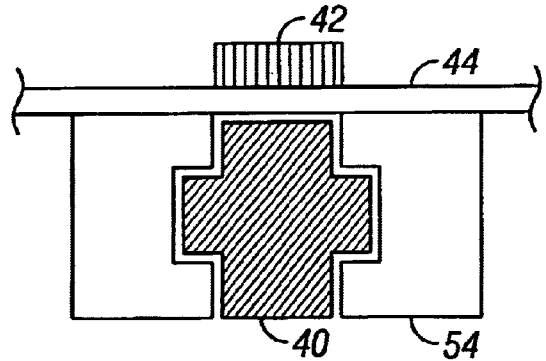
FIG. 5G    FIG. 5H

MAGNETIC ANCHORING DEVICES

FIELD OF THE INVENTION

The present invention relates generally to medical devices and methods. More particularly, the present invention relates to devices and methods for the magnetic attachment of expandable devices and the like within a patient's body cavity, such as the stomach, intestine or gastrointestinal tract.

BACKGROUND OF THE INVENTION

In cases of severe obesity, patients may undergo several types of surgery either to tie off or staple portions of the large or small intestine or stomach, and/or to bypass portions of the same to reduce the amount of food desired by the patient, and the amount absorbed by the intestinal tract. Procedures such as laparoscopic banding, where a device is used to "tie off" or constrict a portion of the stomach, or placement of intragastric balloons, can achieve these results.

Endoscopic procedures that have been used to assist weight loss have primarily focused on placement of a balloon or other space-occupying device in the patient's stomach. This fills portions of the stomach and provides the patient with a feeling of fullness, thereby reducing food intake. To accomplish these procedures, an endoscope is utilized to guide the balloon through the patient's mouth and down the esophagus to the stomach. Usually these procedures have allowed placement of the device for 3–6 months, and are coupled with counseling and other types of behavioral modification programs.

Many of the conventional surgical interventions require the patient to submit to an intervention under general anesthesia, and can require large incisions and lengthy recovery time. The less invasive procedures, although clinically efficacious in many cases, suffer from complications ranging from deflation of the devices to insufficient anchoring of these devices resulting in unsustained weight loss, stomach erosion, bowel obstruction and even death.

Many of these devices are neither robust enough nor are they adequately secured within the stomach to sustain long term implantation. As a result, many implanted devices are implanted in such a manner as to remain unattached or free-floating within the stomach. Further, due to the caustic nature of stomach acids and other factors, many of the implants deflate and migrate into the intestine, causing bowel obstructions and in some cases death. Also, many devices are not well designed for removal, leading to additional technical difficulties for the clinician.

BRIEF SUMMARY OF THE INVENTION

The present invention provides improved methods and apparatus for implanting and anchoring space-occupying devices into the gastrointestinal system of a patient, e.g., the stomach of the patient, which can be deployed in a minimally invasive manner such as transesophageal endoscopy. The invention allows greater access to procedures and devices by patients who might not otherwise be treated surgically as "morbidly obese" (at or above a Body Mass Index (BMI) of 40 kg/m3), but who may just be moderately obese or overweight (BMI of between 25 to 40 kg/m3). In addition, patients who require more invasive surgery for an unrelated ailment, may need a minimally invasive way to lose the weight prior to their more invasive procedure, thereby reducing the risks associated with general anesthesia, or otherwise enabling the more invasive procedure.

Expandable devices that may be inserted into the stomach of a patient may be maintained within the stomach by anchoring or otherwise fixing the device to the stomach wall of the patient. Such expandable devices, e.g., an inflatable balloon, may comprise two portions, an inner portion and an outer portion, the inner portion being able to maintain its shape, regardless of the integrity of the outer portion. Other expandable balloon devices may be used to maintain their expanded shape and desired volume, independent of any small leaks that may develop over time, or they may be configured to maintain a volume of the space-occupying device that can be adjusted in-situ, to change the size of the device after implantation.

The space-occupying devices may be anchored to the stomach wall by an anchoring device that may comprise one or more proximal magnetic devices for magnetically coupling with a distal magnetic anchor located on the stomach wall. The magnetic device and anchor may both be magnets or portions of magnetizable material. Similarly, the proximal magnetic device may be a magnet or portion of magnetizable material while the distal magnetic anchor may be a magnet of opposite polarity, or a magnetically attractive metal. Alternatively, the proximal device may be a magnetically attractive metal and the distal anchor may be a magnet.

The magnetic device may be affixed to the space-occupying member, or may be movable within the member and directable to the site of attachment at the stomach wall by magnetic attraction. The magnetic device may be completely within the space-occupying member. On the other hand, the magnetic device may be positioned on an external surface of the space-occupying member or be integral thereto, and be configured such that a portion of it extends at least partially through one or several folds of the patient's stomach wall, thereby maintaining the device within the patient's stomach.

As will soon become apparent, the magnetic device and anchor may take any variety of configurations and be made of any number of materials. Similarly, the device and anchor may have a variety of different surfaces. They may be textured, or have a detent. In this way, adequate perfusion of tissue is accomplished and ischemic tissue necrosis is prevented. Any number of coupling devices may be used.

BRIEF DESCRIPTION OF THE DRAWINGS

FIGS. 5D through 5H show variations of the present invention in which the magnetic device is used with a toroidal space-occupying member.

DETAILED DESCRIPTION OF THE INVENTION

Figure 1:
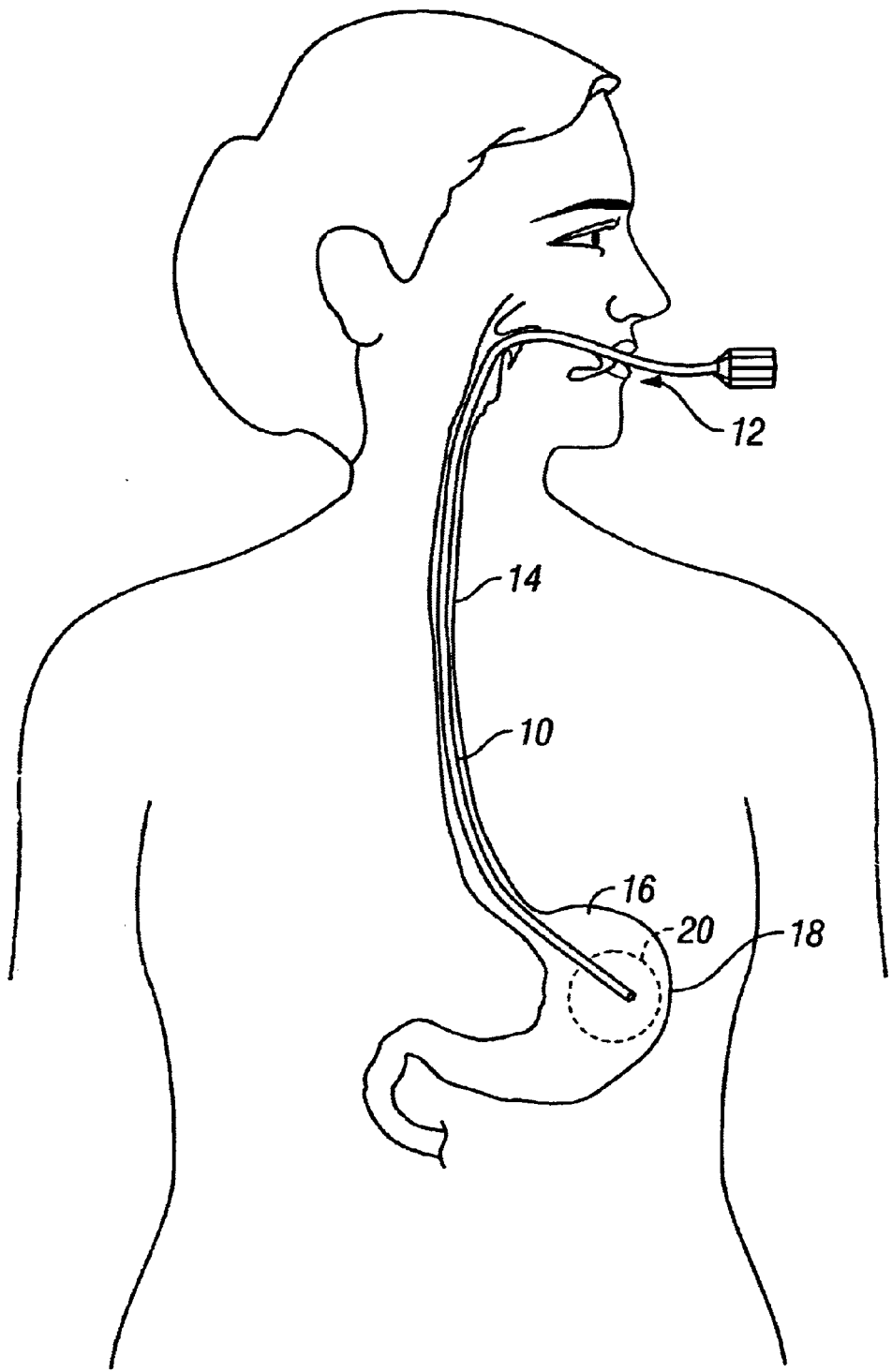
FIG. 1 shows a schematic illustration of a delivery endoscope advanced to a region of interest within the stomach of a patient.

Expandable devices may be inserted into the stomach of a patient and be attached to the stomach walls by magnetic anchoring devices. Although the magnetic anchoring devices disclosed herein describe attachment to the stomach walls, the anchors may be utilized in any hollow body organ or interior body space for temporarily or permanently anchoring expandable devices to tissue. The description herein of use of the magnetic coupling device with a stomach wall is merely illustrative. FIG. 1 illustrates a delivery endoscope 10 that may be used to deliver the expandable devices into, e.g., stomach 18 of a patient. Endoscope 10 is shown as having been advanced through the mouth 12 and esophagus 14 of the patient to position the distal end of endoscope 10 within a region of interest 20 within stomach 16.

Figure 2A:
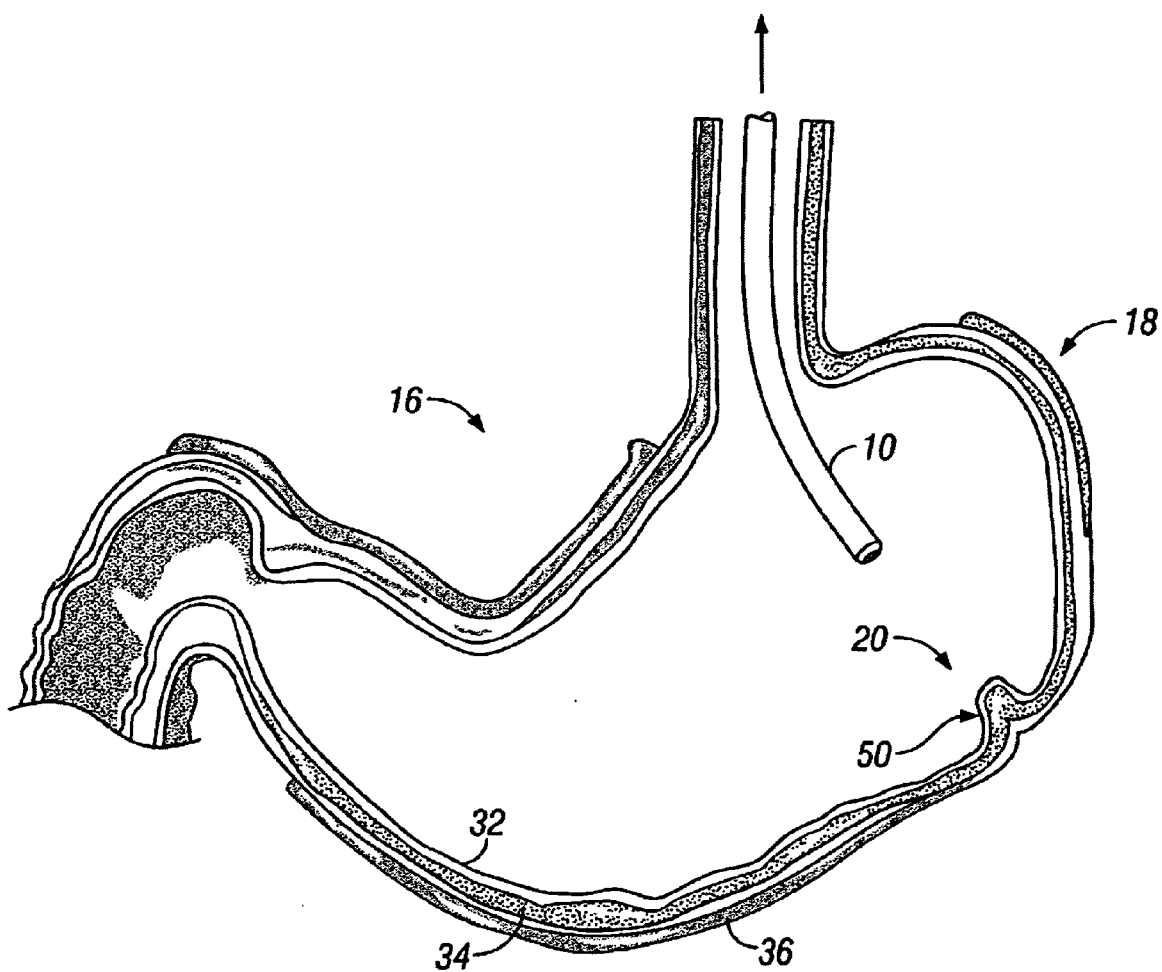
FIG. 2A shows a cross-sectional view of a stomach within which a tissue fold has been formed from the walls of the stomach.

FIG. 2A shows a cross-sectional view of stomach 16 within which endoscope 10 has been positioned adjacent to the region of interest 20. Any number of conventional tools may be passed through the working channel of endoscope 10, or any of the tissue acquisition devices as described in further detail in U.S. patent application Ser. No. 09/871,297 filed May 30, 2001 or U.S. patent application Ser. No. 10/188,547 filed Jul. 2, 2002, both of which are commonly owned and are incorporated herein by reference in their entirety.

Figure 2B:
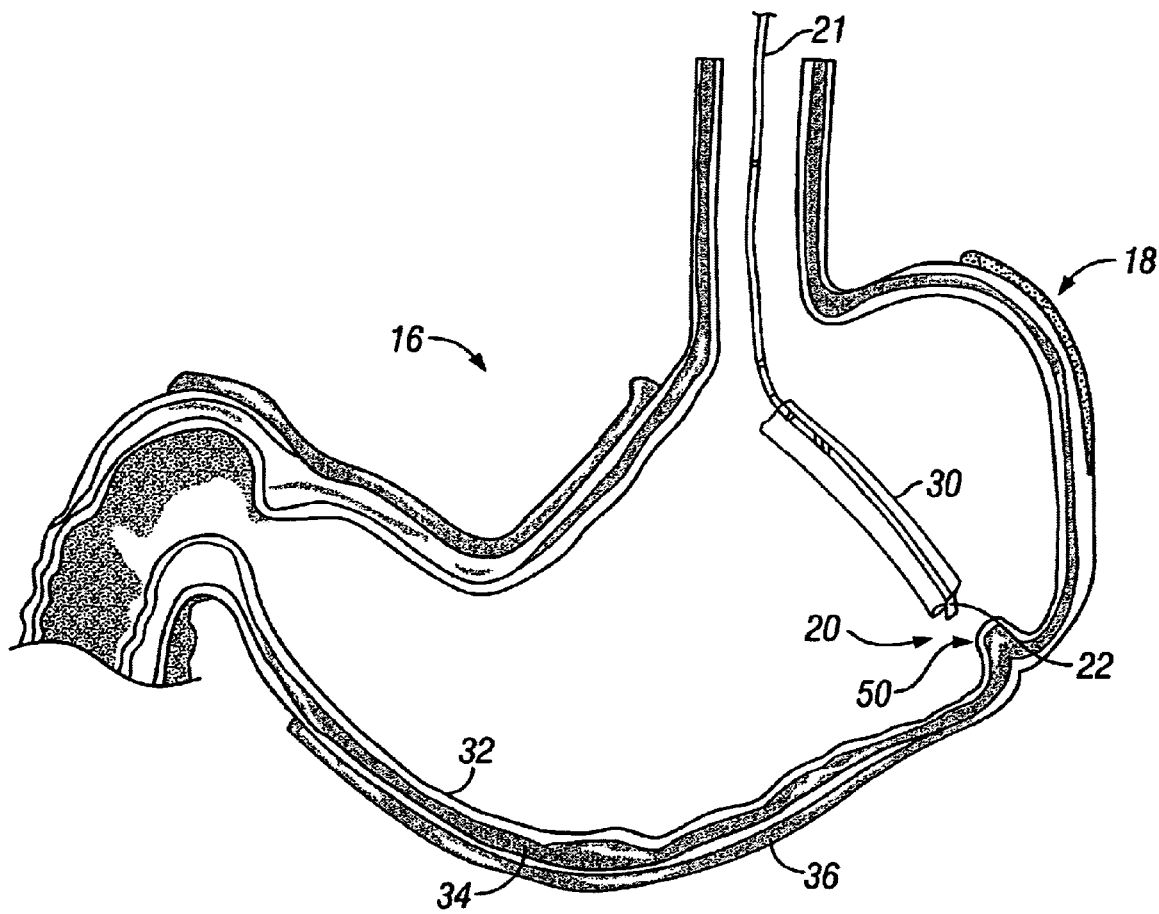
FIG. 2B shows the stomach of FIG. 2A in which an inflatable or space-occupying member (in its deflated or unexpanded state) has been advanced for anchoring to the tissue fold.

The space occupying device, e.g., an expandable scaffold, an inflatable balloon, etc., may be advanced within stomach 16 towards the region of interest 20 for anchoring to the stomach wall. As shown in FIG. 2B, space-occupying member 30 may be advanced using an elongate delivery member 21, e.g., endoscope 10 or any one of the delivery devices as shown and described in U.S. patent application Ser. No. 09/816,850 filed Mar. 23, 2001, which is commonly owned and is incorporated herein by reference in its entirety. The use of an inflatable balloon in these examples is intended to be illustrative and any number of space-occupying devices, such as an expandable scaffold, may be utilized as described in the incorporated application.

Figure 3:
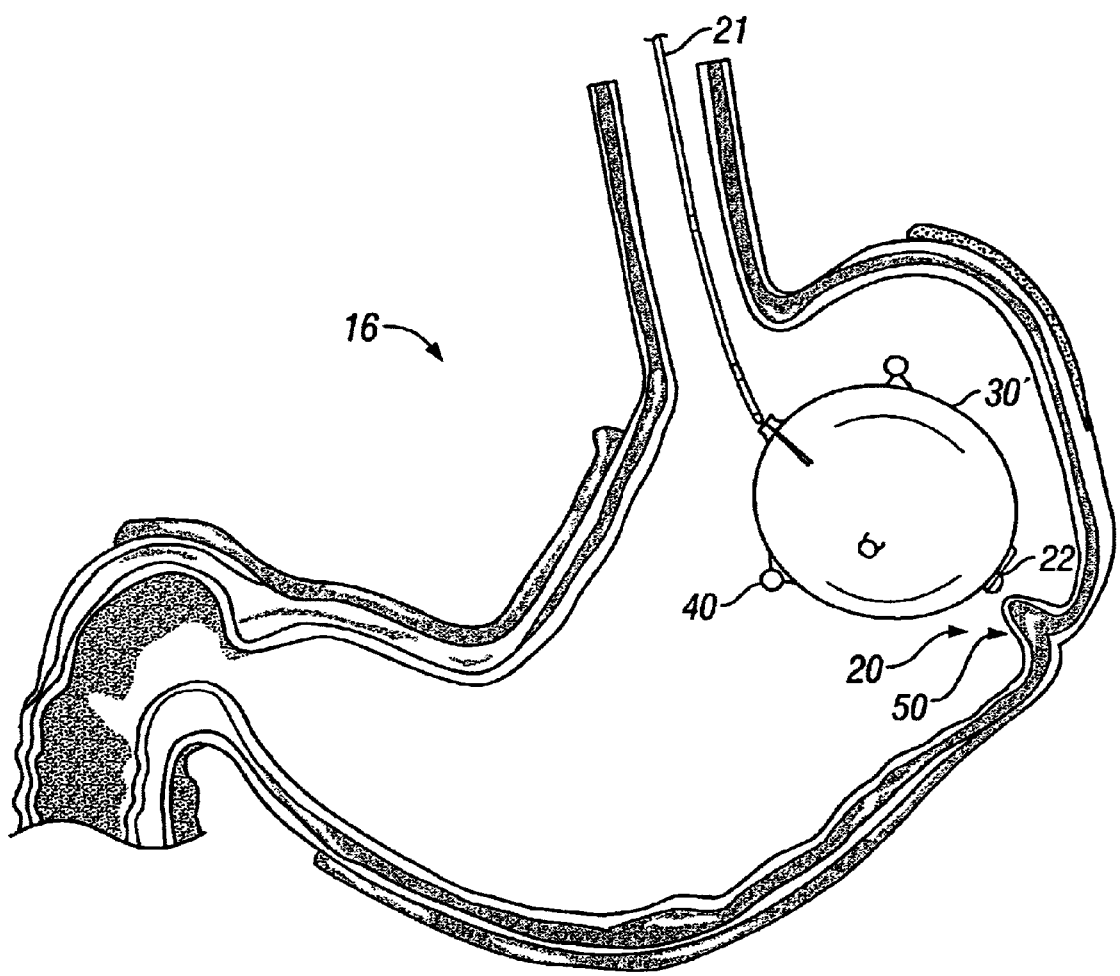
FIG. 3 shows the stomach of FIGS. 2A and 2B in which the space-occupying member has been expanded for deployment.

As seen in FIG. 3, delivery member 21 may be used to inflate space-occupying member 30 into its expanded shape 30'. The surface of space-occupying member 30' may have one or several tabs 40 extending from or defined along its outer surface to allow a grasping tool to manipulate or remove space-occupying member 30' during the procedure or post-procedurally.

Space-occupying member 30 may be formed of a urethane interior and a silicone exterior. The urethane provides durability to the balloon for resisting undesirable rupture or leakage and the silicone exterior provides for smoothness and conformability, to avoid unnecessary trauma or irritation to the stomach lining. In another variation, the member 30 is formed of a composite of silicone, aluminized polyester film, and polyethylene. In this variation, the space occupying device is formed by heat-sealing sheets of mylar/polyethylene composite. The seam is then trimmed to a minimum size and a valve attached. The assembly is then dipped in room temperature vulcanizing (RTV) liquid silicone which, once cured, will leave a smooth surface, which may or may not have a palpable seam. Alternatively, the space-occupying device can be rotated as the silicone cures, to allow for a more consistent coating to form.

A variety of sizes and shapes of space-occupying member 30 are contemplated, and it is to be appreciated that one skilled in the art would be competent to choose a particular shape and size according to the particular application. The space-occupying member 30 can be, for example, a spherical or ellipsoidal balloon or another suitable shape. In the case of an ellipsoidal balloon, one method of anchoring such a balloon is along the longer axis of the balloon; however, anchoring may also be achieved by anchoring along the shorter axis of the balloon. Balloon volumes can vary, but a typical volume is approximately 500 cubic centimeters (cc).

Figure 4A:
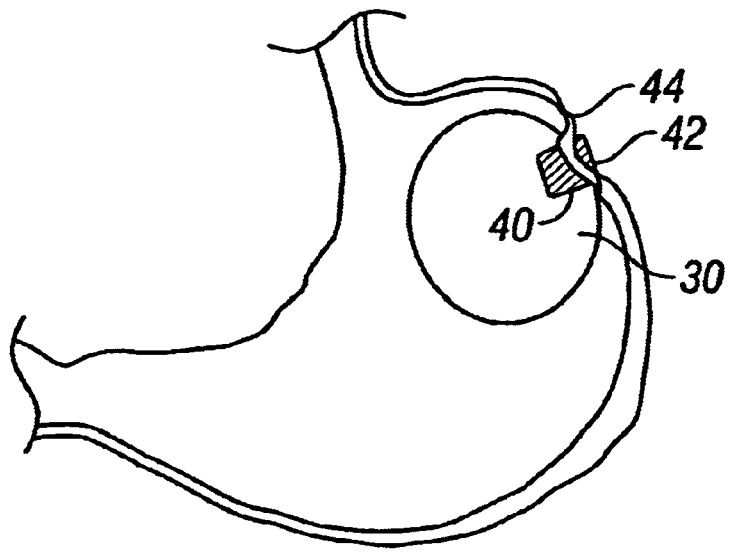
FIG. 4A shows one variation of the space-occupying member where the magnetic device is affixed thereto and is magnetically coupled to the magnetic anchor on the stomach wall.

One variation of space-occupying member 30 is shown in FIG. 4A. In this variation, the space-occupying member comprises at least one proximal magnetic device 40 for magnetically coupling with a distal magnetic anchor 42 affixed to the stomach wall 44. The magnetic device and anchor may be magnets or portions of a magnetizable material. Similarly, the proximal magnetic device may be a magnet or portion of magnetizable material while the distal magnetic anchor may be a magnet of opposite polarity, or a magnetically attractive metal. Alternatively, the proximal device may be a magnetically attractive metal and the distal anchor may be a magnet.

The magnetic device and anchor should be resilient and provide strong enough magnetic forces, approximately ½ $lb_f$ to 2 $lb_f$, to result in magnetic coupling across the stomach wall, but not be so strong as to traumatize the surrounding tissue, cause ischemia, or pressure necrosis. The attachment of the space-occupying member to the stomach wall may be accomplished prior to, during, or even after inflation or expansion of member 30 and may be done by any number of manipulation tools endoscopically or laparoscopically delivered and positioned, as appreciated by one skilled in the art.

Figure 4B:
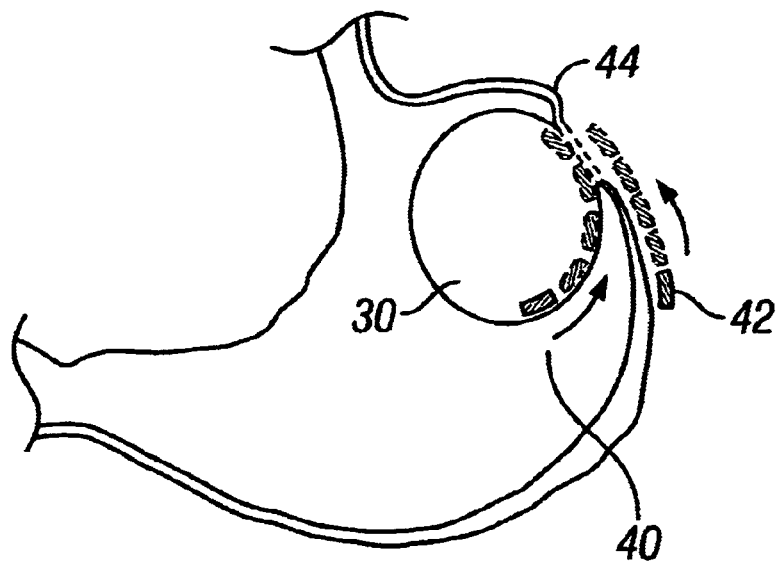
FIG. 4B shows another variation of the space-occupying member where the magnetic device is un-affixed thereto and is movable to the site of attachment with the magnetic anchor on the stomach wall.

The magnetic device of the space-occupying member may or may not be affixed thereon. For example, as shown in FIG. 4B, the magnetic device 40 may be non-affixed and be movable to the site of attachment just prior to attachment. This may be accomplished by using the magnetic anchor 42 to be affixed to the stomach wall 44 to attract mobile magnetic device 40 and pull it to the site of attachment.

Movement of the mobile magnetic device 40 may also be accomplished by any other similar magnetic attraction means.

Figure 5A:
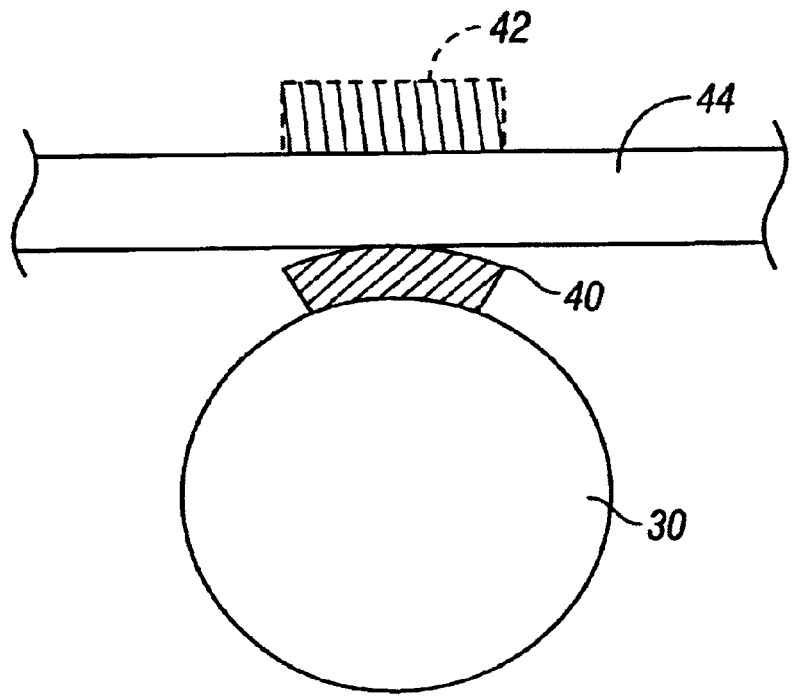
FIG. 5A shows one variation where the magnetic device of the present invention is positioned on an external surface of the space-occupying member.
Figure 5B:
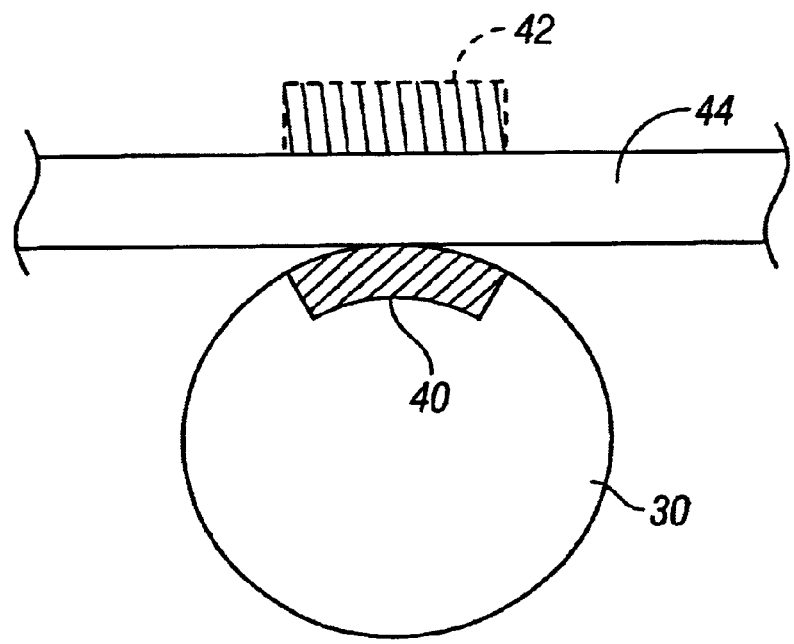
FIG. 5B shows another variation where the magnetic device of the present invention is positioned on an internal surface of the space-occupying member.
Figure 5C:
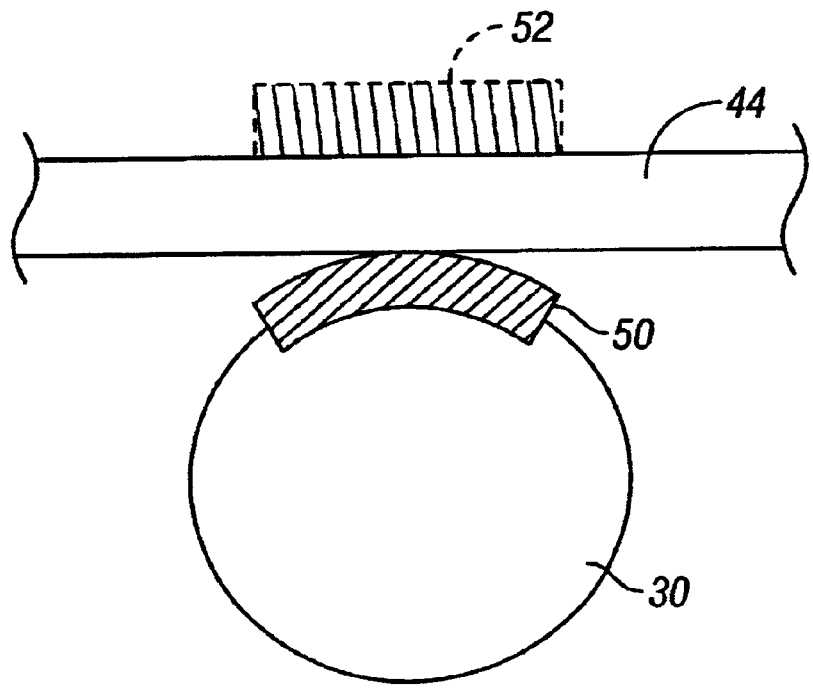
FIG. 5C shows yet another variation where the space-occupying member comprises an integral magnetic device.
Figure 5D:
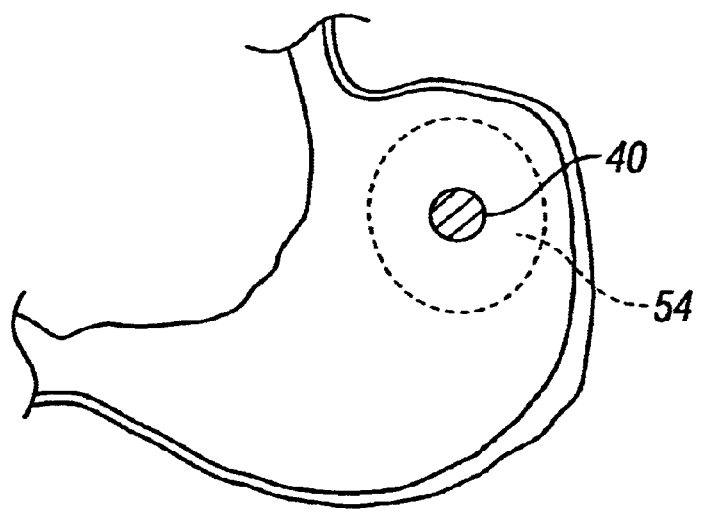

The magnetic device may be positioned on an external surface of the space-occupying member or may be positioned on its internal surface as shown in FIGS. 5A and 5B respectively. In one variation, shown in FIG. 5C, the space-occupying member itself comprises integral magnetic device 50, having an external magnetic, magnetizable or metallic surface 52. In another variation, shown in FIGS. 5D through 5H, the magnetic device and anchor of the present invention are used in combination with a toroidal space-occupying member. FIG. 5D illustrates toroidal space-occupying member 54 positioned within a stomach, and magnetic device 40 positioned within an opening of the toroidal spaceoccupying member 54. The toroidal space-occupying member may have any number of configurations and the magnetic device may have any number of corresponding configurations, adaptable to the opening of the toroidal space-occupying member. For example, toroidal space-occupying member 54 may a uniform inner circular circumference, or may instead, have a non-uniform inner circumference. A few illustrative variations are provided in FIGS. 5E through 5H. The magnetic devices may be extremely flexible or rigid, or have any tensile strength therebetween.

The magnetic anchor of the stomach wall may be made of a biocompatible material or be coated with a material, eg. silicone, to achieve biocompatability. Similarly, when the magnetic device is external or integral to the space-occupying member, as shown in FIGS. 5A and 5D respectively, any surface exposed to the body should be made biocompatible.

Several methods may be used to secure or place the magnetic anchor on a surface on the stomach wall. For example, portions of the stomach are accessible via minimally invasive surgery. The stomach may be accessed via the abdominal wall, under the lower ribs on the left side, or under the left lobe of the liver. Any of these access sites may be selected depending on the desired placement of the magnetic anchor.

One method of attaching the magnetic anchor to the stomach wall is laparoscopically. Using this method, a thin, telescope-like instrument (e.g., a laparoscope) is inserted through a small incision at the umbilicus (belly button). The laparoscope is connected to (or comprises) a tiny video camera, which projects a view of the abdomen onto a video monitor located in the operating room. Sometimes the abdomen is inflated with a gas (e.g., carbon dioxide).

Several additional small incisions (e.g., four to five depending on the particular surgical needs) are then made near the site of the laparoscope. Through these incisions, the surgeon may insert instruments for maneuvering the magnetic anchor and suturing it to the stomach wall. Similarly, any other instruments necessary for facilitating the attachment of the magnetic anchor to the stomach wall may be inserted through these incisions. After the magnetic anchor is attached to the stomach wall, the small incisions are closed with sutures and covered with a protective bandage.

Another method of attaching the magnetic anchor to the stomach wall makes use of small incisions, without using the laparoscopic method. Simple incisions may be made while the patient is under local anesthesia for accessing the stomach wall and for affixing the magnetic anchor thereto. If the patient prefers, general anesthesia may be administered. However because the incisions will be small (not the 8–10 inch incisions typically performed in most "open" surgeries), recovery time and scarring will be minimal.

For example, a small incision may be made in the linea alba by a downward cut from the ensiform cartilage. The peritoneal cavity may then be opened. The stomach is now accessible for affixing the magnetic anchor. The anchor itself may comprise a portion to allow for suturing to the stomach wall, or may have an aperture for suturing therethrough. Any number of anchor configurations may be selected. Once the anchor configuration has been selected, the method of physically securing it to the stomach wall will become readily apparent to those skilled in the art. Of course, if the laparoscopic or simple incision methods prove unsuccessful during surgery itself, the traditional "open surgery" method may be used to attach the magnetic anchor to the stomach wall.

Similarly, any number of methods may be used to affix the magnetic device to the space-occupying member when it is desirable to have the device affixed thereto. The appropriate securing method may depend on the material comprising the space-occupying member and on whether the device is to be affixed to an external or internal surface. This is because the body may be unable to break down certain substances and their introduction into the body may pose serious health risks. However, when the device is to be affixed to an internal surface of the space-occupying member, a variety of different adhesives, glues, cements, resins, bonding agents, or other methods may be used. However, special care must be taken to select a securing agent that is non-corrosive and that will not degrade or permeate the space-occupying member.

Figure 6A:
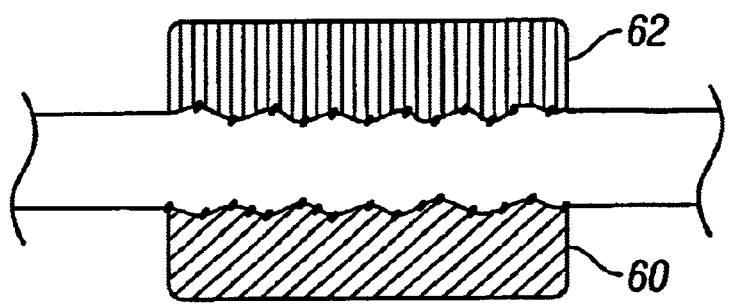
FIG. 6A shows one variation where the surfaces of the magnetic device and anchor are textured.
Figure 6B:
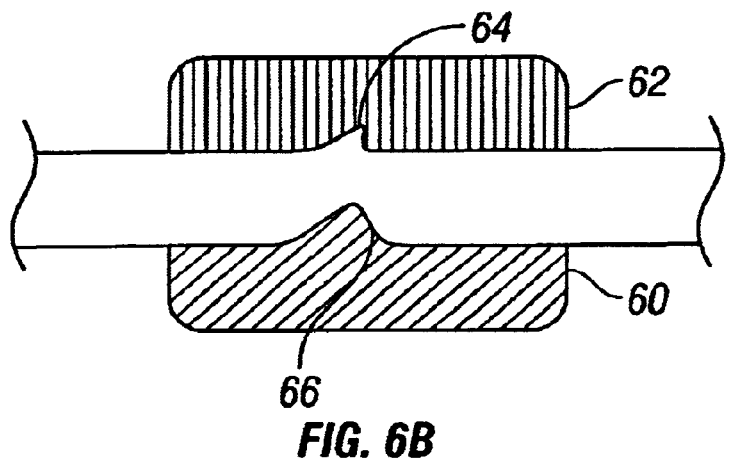
FIG. 6B shows another variation where the magnetic anchor comprises at least one detent for receiving at least one protruding portion of the magnetic device.
Figure 6C:
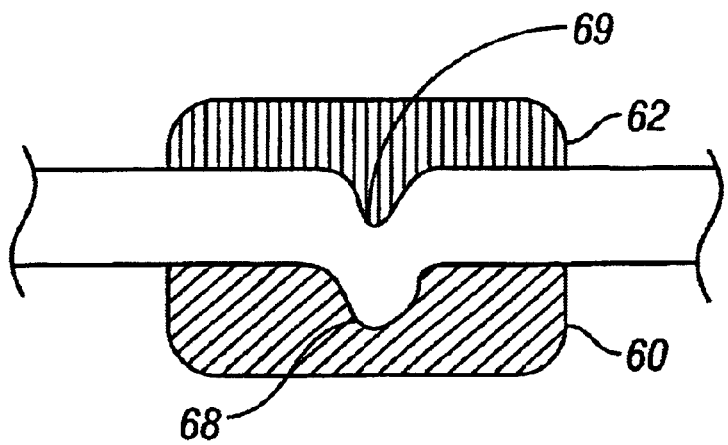
FIG. 6C shows another variation where the magnetic device comprises at least one detent for receiving at least one protruding portion of the magnetic anchor.

FIG. 6A shows one variation where the proximal magnetic device 60 and distal magnetic anchor 62 have textured surfaces. This may help facilitate coupling and also help prevent slippage of the space-occupying member. In addition, having a texture or tread allows for adequate perfusion of the tissue and helps prevent ischemic tissue necrosis. Similarly, the magnetic device or anchor may comprise at least one detent for receiving at least one protruding portion of the corresponding device or anchor as shown in FIGS. 6B and 6C. In FIG. 6B, distal magnetic anchor 62 has detent 64 for receiving protruding portion 66 of proximal magnetic device 60. Similarly, in FIG. 6C,.proximal magnetic device 60 has detent 68 for receiving protruding portion 69 of distal magnetic anchor 62.

In another variation a tissue fold may be utilized. As illustrated in FIG. 2, the tissue layers of stomach 16 are comprised of the mucosal layer 32, the muscularis or fibrous muscular layer 34, and the serosal layer 36. In forming tissue fold 50, at least two layers of stomach tissue are folded to contact itself such that a certain amount of fibrous tissue overlap occurs prior to fastening tissue fold 50 in a configuration akin to a lap joint. The amount of the overlap can vary and needs only be sufficient enough to result in joining of the fastened sections, thereby creating a tissue bridge along the length of the fastened tissue. Formation of tissue folds was described in detail in U.S. patent application Ser. No. 10/215,070 filed on Aug. 7, 2002 which is commonly owned and incorporated herein by reference in its entirety.

Figure 7A:
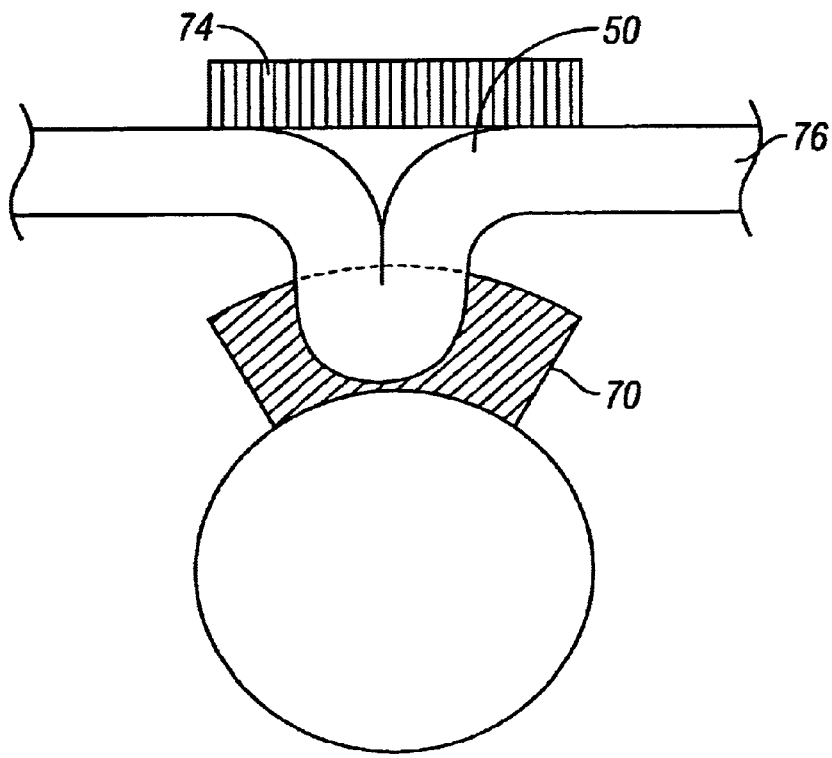
FIG. 7A shows how a portion of the magnetic device may be positioned through a tissue fold when the magnetic device is on an external surface of the space-occupying member.
Figure 7B:
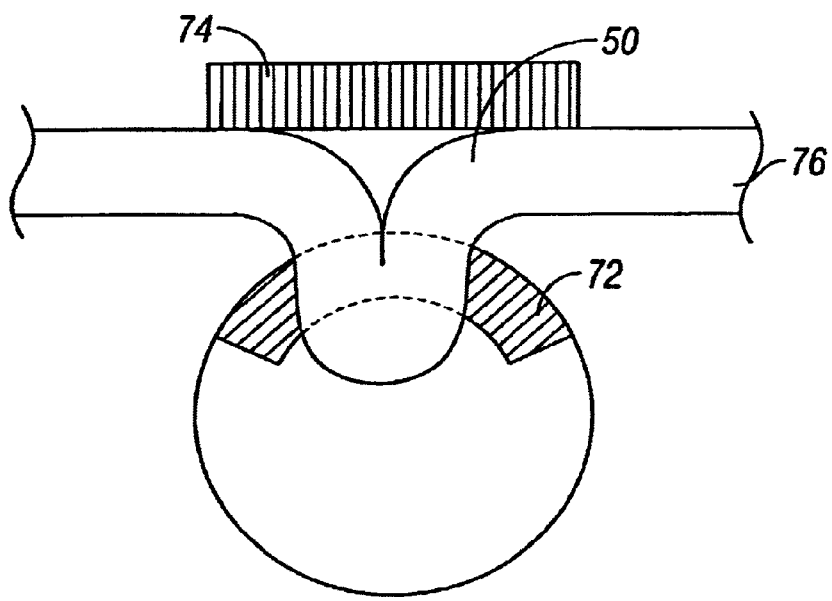
FIG. 7B shows how a portion of the magnetic device may be positioned through a tissue fold when the space-occupying member comprises an integral magnetic device.

The tissue bridge may be formed of various layers of the stomach and may include scar tissue and other elements of effective wound healing. Once tissue fold 50 has been desirably configured, a portion of the magnetic device may be positioned therethrough for maintaining the tissue fold configuration. For example, as shown in FIGS. 7A and 7B, when the magnetic device is on the external surface of space-occupying member 70 or integral thereto 72, a portion of it may be inserted through the tissue fold. Magnetic anchor 74 on stomach wall 76 is then positioned on a corresponding surface distal thereto for coupling with the magnetic device.

Any number of such tissue folds as practicable may be used depending upon the desired results and anchoring configuration. Similarly, any number of magnetic coupling devices may be used. For example, in some instances it may be desirable to magnetically couple the space-occupying member to the stomach wall at more than one point of attachment. This may provide extra stability to the space-occupying member and also help prevent its migration or detachment in the event that one set of magnetic coupling device and anchor becomes loose. In this way, the prior art problems of inadequately secured devices may further be reduced or eliminated.

Although illustrative variations of the present invention are described above, it will be evident to one skilled in the art that various changes and modifications may be made without departing from the invention. For instance, variations of the present invention may be used as permanent or temporary anchoring devices. Moreover, modified variations may also be used in other regions of the body, e.g., for use in the intestinal tract, etc. It is intended in the following claims to cover all such changes and modifications that fall within the true spirit and scope of the invention.

We claim:

1. A method of anchoring an inflatable device to a region of tissue within a stomach, comprising:
   providing an inflatable device comprising at least one magnetic devices;
   securing at least one magnetic anchor to a surface of a stomach;
   magnetically coupling the at least one magnetic device with the at least one magnetic anchor such that the inflatable device is secured against a region of tissue within the stomach.

2. The method of claim 1 further comprising advancing an endoscope transorally to the region of tissue.

3. The method of claim 1 wherein the at least one magnetic device is selected from the group consisting of a magnet, a magnetizable material, and a magnetic metal.

4. The method of claim 1 wherein the at least one magnetic anchor is selected from the group consisting of a magnet, a magnetizable material, and a magnetic metal.

5. The method of claim 1 wherein the magnetic device is unaffixed to the inflatable device.

6. The method of claim 1 wherein the magnetic device is integral to the object.

7. The method of claim 1 wherein the magnetic device is positioned on an external surface of the inflatable device.

8. The method of claim 1 wherein the surfaces of the magnetic device and anchor are textured.

9. The method of claim 1 wherein the at least one magnetic anchor has at least one protruding portion and the at least one magnetic device has at least one detent for receiving the at least one protruding portion.

10. The method of claim 1 wherein the at least one magnetic device has at least one protruding portion and the at least one magnetic anchor has at least one detent for receiving the at least one protruding portion.

11. The method of claim 1 further comprising:
    configuring the region of tissue to create at least one fold of tissue; and
    positioning a portion of the at least one magnetic device therethrough.

12. A stomach volume occupying system comprising:
    an inflatable device having at least one magnetic device; and
    at least one magnetic anchor positioned on a surface of a stomach, wherein the magnetic device of the inflatable device may be magnetically coupled to the magnetic anchor such that the inflatable device is attached to an interior surface of the stomach.

13. The system of claim 12 wherein the inflatable device is configured to expand to a predetermined volume.

14. The system of claim 12 wherein the inflatable device comprises an inflatable balloon.

15. The system of claim 14 wherein the inflatable balloon is toroidal.

16. The system of claim 12 wherein the at least one magnetic device is selected from the group consisting of a magnet, a magnetizable material, and a magnetic metal.

17. The system of claim 12 wherein the at least one magnetic anchor is selected from the group consisting of a magnet, a magnetizable material, and a magnetic metal.

18. The system of claim 12 wherein the magnetic device is unaffixed to inflatable device.

19. The system of claim 12 wherein the magnetic device is integral to the inflatable device.

20. The system of claim 12 wherein the magnetic device is positioned on an external surface of the inflatable device.

21. The system of claim 12 wherein the surfaces of the magnetic device and anchor are textured.

22. The system of claim 12 wherein the at least one magnetic anchor has at least one protruding portion and the at least one magnetic device has at least one detent for receiving the at least one protruding portion.

23. The system of claim 12 wherein the at least one magnetic device has at least one protruding portion and the at least one magnetic anchor has at least one detent for receiving the at least one protruding portion.

* * * * *